United States Patent [19]

Lee et al.

[11] Patent Number: 4,921,526

[45] Date of Patent: May 1, 1990

[54] SUBSTITUTED BICYCLOAKLY-1,3-DIONES

[75] Inventors: Shy-Fuh Lee, Sunnyvale; Gary W. Luehr, Mountain View; Carol R. Scott, Newark, all of Calif.; Werner Trueb, Therwil, Switzerland

[73] Assignee: Sandoz Ltd., Basel, Switzerland

[21] Appl. No.: 125,843

[22] Filed: Nov. 27, 1987

[51] Int. Cl.$^5$ ............................................. A01N 57/00
[52] U.S. Cl. .......................................... 71/86; 71/87; 71/103; 71/105; 71/107; 71/114; 71/115; 71/118; 71/121; 71/122; 71/123; 558/45; 558/57; 558/61; 558/62; 558/193; 558/198; 558/209; 558/214; 558/386; 558/414; 560/117; 560/119; 562/499; 562/502; 564/162; 564/169; 564/308

[58] Field of Search ...................... 71/86, 87, 103, 105, 71/107, 114, 115, 118, 121, 122, 123; 558/45, 57, 61, 62, 193, 198, 209, 214, 386, 414; 560/117, 119; 562/499, 502; 564/162, 169, 308

[56] References Cited

U.S. PATENT DOCUMENTS 2,820,738  1/1958  Litvan et al. ........................ 568/327

FOREIGN PATENT DOCUMENTS 8652992  8/1986  Australia .

*Primary Examiner*—Robert A. Wax
*Attorney, Agent, or Firm*—Allen E. Norris

[57]  ABSTRACT

Substituted benzoyl-bicycloalkyl-1,1,3-diones and related compounds, intermediates therefor, synthesis thereof, and the use of said diones for the control of weeds.

12 Claims, No Drawings

SUBSTITUTED BICYCLOAKLY-1,3-DIONES

This invention relates to novel substituted benzoylbicyclo-1,3-diones and related compounds, intermediates therefor, synthesis thereof, and the use of said compounds for the control of weeds.

More particularly, the compounds of the present invention are represented by the following formula (I):

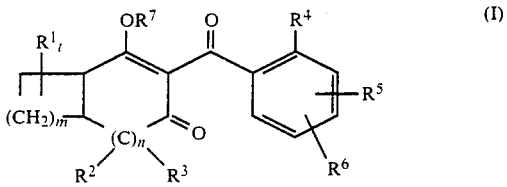

wherein, $R^1$ is $C_{1-8}$alkyl;

each of $R^2$ and $R^3$ is, independently, hydrogen, $C_{1-8}$alkyl or $COOR^8$;

$R^4$ is $C_{1-8}$alkyl, optionally substituted with one to six halogen atoms; $C_{1-8}$alkoxy, optionally substituted with one to six halogen atoms; $S(O)_{n'}R^{10}$; halogen; or nitro;

each of $R^5$ and $R^6$ is, independently, hydrogen; halogen; $C_{1-8}$alkyl, optionally substituted with one to six halogen atoms; $C_{1-8}$alkoxy, optionally substituted with one to six halogen atoms; $C_{1-8}$alkylcarbonyl; $C_{1-8}$alkoxycarbonyl; $NR^8R^9$; $SO_2NR^8R^9$; $S(O)_{n'}R^{10}$; nitro; or cyano; with the proviso that neither of $R^5$ nor $R^6$ is attached to the 6 position;

$R^7$ is hydrogen, $C_{1-8}$alkyl, $C_{1-8}$alkylcarbonyl, $C_{1-8}$alkoxycarbonyl, $C(O)NR^8R^9$, $C_{1-8}$alkylsulfonyl, $P(O)(OR^{11})_2$ or $R^8P(O)OR^{11}$;

each of $R^8$ and $R^9$ is, independently, hydrogen or $C_{1-8}$alkyl;

$R^{10}$ is $C_{1-8}$alkyl, optionally substituted with one to six halogen atoms;

$R^{11}$ is $C_{1-8}$alkyl;

m is zero to three;

n is zero or one;

n' is zero, one or two; and t is zero to six.

In the description and claims hereinafter, each of m, n, n', t and $R^1-R^{11}$ is as defined above, unless otherwise specified.

In the practice of the present invention, m is preferably two or three.

Where any of the substituents $R^4-R^6$ and $R^{10}$ is or comprises halogen, such halogen is conveniently selected from bromo, chloro and fluoro.

Where any of $R^1-R^{11}$ is or comprises $C_{1-8}$alkyl, it is preferably of one to four carbons.

Where any of $R^4-R^7$ is or comprises $C_{1-8}$alkoxy, it is preferably of one to four carbons.

Each of $R^2$ and $R^3$ is preferably hydrogen or $C_{1-4}$alkyl; such alkyl is more preferably of one to three carbons.

$R^4$ conveniently signifies $C_{1-4}$alkyl, optionally substituted with halogen; $C_{1-4}$alkyl-$S(O)_{n'}$; halogen; or nitro. It is preferably methyl, $CF_3$, $C_{1-3}$alkylsulfonyl, chloro, bromo or nitro.

$R^5$ conveniently signifies hydrogen; $C_{1-4}$alkyl optionally substituted with halogen; $C_{1-4}$alkyl-$S(O)_{n'}$ optionally substituted with halogen; $C_{1-4}$alkoxy optionally substituted with halogen; halogen; or nitro. It is preferably hydrogen, $CF_3$, $C_{1-3}$alkylsulfonyl, chloro$C_{1-3}$alkylsulfonyl, methoxy, chloro, fluoro or nitro.

$R^5$ is preferably in the 4-position.

$R^6$ is preferably hydrogen.

$R^7$ is conveniently hydrogen, $C_{1-4}$alkyl, $C_{1-4}$alkylcarbonyl or $C_{1-4}$alkylsulfonyl. It is preferably hydrogen, methyl, ethyl, methylcarbonyl, ethylcarbonyl or methylsulfonyl; it is more preferably hydrogen.

The compounds of the present invention of formula I are new substances which can be prepared by methods analogous to methods known in the art, such as those described in European Patent Application EP 186,117 and references cited therein. More particularly, they can be obtained by, for example: reacting an enol ester of formula (IIa) or (IIb)

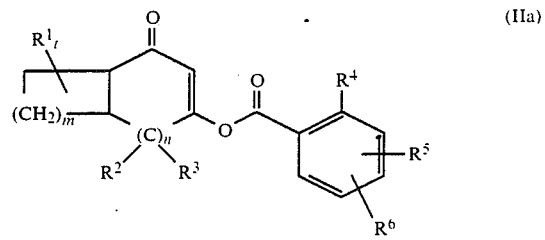

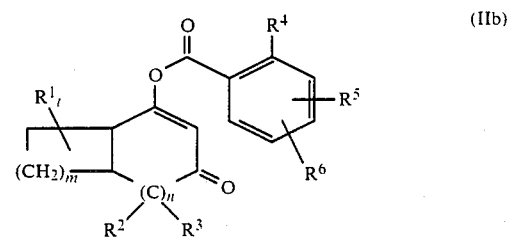

wherein m, n, t and $R^1-R^6$ are as defined above, with a cyanide source and a moderate base to give a compound of formula I where $R^7$ is hydrogen.

The above reaction is carried out in the presence of a catalytic amount of a source of cyanide anion and/or hydrogen cyanide, together with a molar excess, with respect to the enol ester, of a moderate base. The reaction is conveniently carried out in a solvent which is inert under the reaction conditions, e.g. 1,2-dichloroethane, toluene, acetonitrile, methylene chloride, ethyl acetate, dimethylformamide (DMF) and methyl isobutyl ketone (MIBK). In general, depending on the nature of the reactants and the cyanide source, the rearrangement may be conducted at temperatures up to about 80° C. In some cases, for instance when there is a possible problem of excessive by-product formation, the temperatures should be kept at about 40° C. maximum.

Preferred cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; cyanohydrins of benzaldehyde or of $C_2-C_5$ aliphatic aldehydes such as acetaldehyde, propionaldehyde, etc., cyanohydrins; zinc cyanide; tri(lower alkyl) silyl cyanides, notably trimethyl silyl cyanide; and hydrogen cyanide itself. Among cyanohydrins the preferred cyanide source is acetone cyanohydrin. The cyanide source is used in an amount up to about 50 mole percent based on the enol ester. Generally about 1–10 mole % of the cyanide source is preferred.

By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this reaction include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate. The base is used in an amount of from about 1 to about 4 moles per mole of enol ester, preferably about 1.3–2 moles per mole.

When the cyanide source is an alkali metal cyanide, particularly potassium cyanide, a phase transfer catalyst may be included in the reaction. Particularly suitable phase transfer catalysts are the Crown ethers.

Compounds of formula I where $R^7$ is other than hydrogen can be prepared by reacting a compound of formula Ia

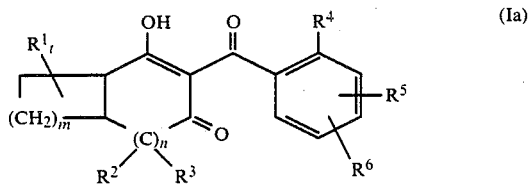

wherein m, n, t and $R^1$–$R^6$ are as defined above, with either
  (a) the group $R^7$-OH and a catalyst, or
  (b) the group $R^7$-Q and a moderate base, wherein Q is a halogen atom and $R^7$ is other than hydrogen, to give a compound of formula I where $R^7$ is as defined above other than hydrogen.

The above reaction (a) is carried out in the presence of a catalyst such as concentrated sulfuric acid. The reaction is conveniently carried out in a solvent which is also the reactant such as methanol, and at an elevated temperature.

The above reaction (b) is carried out in the presence of a moderate base such as triethylamine or pyridine and conveniently at RT or below.

The compounds of formula I may be recovered from the reaction mixture in which they are formed by working up by established procedures.

The starting materials and reagents employed in the process described herein are either known or, insofar as they are not known, may be produced in a manner analogous to the processes described herein or to known processes.

The compounds of this invention wherein $R^7$ = H can have the following four structural formulae because of tautomerism:

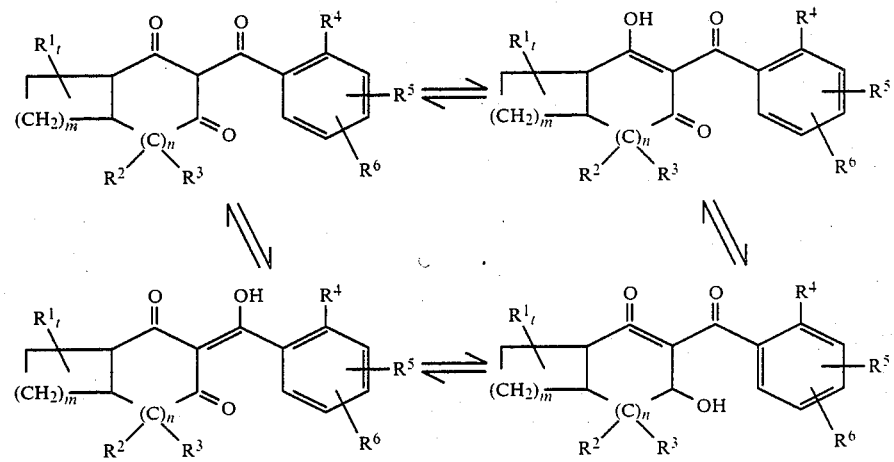

The novel compounds of formula (I) are useful for the control of weeds, using pre- and/or post-emergent treatments. They are also useful as plant growth regulators. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre. The application of a compound of the present invention to the "locus" of the weed includes application to the seeds, the plant (weed) or parts of the plant, or the soil.

The term "herbicide," as used herein, refers to an active ingredient which modifies the growth of plants because of phytotoxic or plant growth regulating properties so as to retard the growth of the plant or damage the plant sufficiently to kill it.

The compounds of the present invention, when applied as either post or pre-emergents, demonstrate high levels of herbicidal activity on broadleaf, grass and sedge weeds.

In the use of the compounds of formula I for combatting weeds, a compound of formula I, or mixtures thereof, can conveniently be employed as herbicidal compositions in association with acceptable diluent(s) for application to the weed or its locus. Such compositions also form part of the present invention.

Methods of preparing herbicidal formulations which can be used with a compound of the present invention are described in the literature along with suitable liquid and solid carriers, such as in U.S. Pat. No. 4,192,669 and 4,163,661, which are incorporated herein by reference.

The optimum usage of a compound of the present invention is readily determinable by one of ordinary skill in the art using routine testing such as greenhouse testing and small plot testing.

Suitable formulations contain from 0.01 to 99% by weight of active ingredient, from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 25% by weight of active ingredient. Lower or higher levels of active ingredient can, of course, be present depending on the intended use, the physical properties of the compound and the mode of application. Concentrate forms of a composition intended to be diluted before use generally contain between 2 and 90%, preferably between 5 and 81% by weight of active ingredient.

Useful formulations of the compounds of formula I include dusts, granules, suspension concentrates, wettable powders, flowables and the like. They are obtained by conventional manner, e.g. by mixing a compound of formula I with the diluent(s) and optionally with other ingredients.

Alternatively, the compounds of formula I may be used in micro-encapsulated form.

The compounds of formula I can be combined with a cyclodextrin to make a cyclodextrin inclusion complex for application to the pest or its locus.

Agriculturally acceptable additives may be employed in the herbicidal compositions to improve the performance of the active ingredient and to reduce foaming, caking and corrosion, for example.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

"Diluent" as used herein means a liquid or solid agriculturally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms e.g. water or diesel oil.

The compositions of this invention can also comprise other compounds having biological activity, e.g. compounds having similar or complementary herbicidal activity for broadspectrum weed control or compounds having antidotal, fungicidal, insecticidal or insect attractant activity.

The following examples are provided to illustrate the practice of the present invention. Temperature is given in degrees Celsius. RT means room temperature. Parts and percentages are by weight.

PREPARATION OF FINAL COMPOUNDS

EXAMPLE 1

To a mixture of 1-(4-chloro-2-nitrobenzoyloxy)-4a,5,6,7,8,8a-hexahydro-3(4H)-naphthalenone and 3-(4-chloro-2-nitrobenzoyloxy)-4a,5,6,7,8,8a-hexahydro-1(4H)-naphthalenone (17.75 g, 50.6 mmol) in 100 ml of acetonitrile is added triethylamine (14.1 ml). Acetone cyanohydrin (2.5 ml) is added and the mixture is stirred overnight at RT. The solvent is removed under vacuum and the residue is dissolved in ether. The solution is washed with 2N HCl, separated and the organic layer is dried. The crude product is purified by chromatography to give 2-(4-chloro-2-nitrobenzoyl)-4a,5,6,7, 8,8a-hexahydro-1,3-(2H,4H)-naphthalenedione, a pure white crystalline solid (compound 1), m.p. 112°.

EXAMPLE 2

Following the procedure of Example 1, each of the final compounds under Column I is prepared by rearrangement of the corresponding enol ester.

I 2. 2-(4-chloro-2-nitrobenzoyl)-4a,5,6,7,8,8a-hexahydro-4-methyl-1,3-(2H,4H)-naphthalenedione, m.p. 87°
3. 5-(4-chloro-2-nitrobenzoyl)-2,3,7,7a-tetrahydro-1H-indene-4,6(5H)-dione, m.p. 107°
4. 5-(4-chloro-2-nitrobenzoyl)-7-methyl-2,3,7,7a-tetrahydro-1H-indene-4,6(5H)-dione, m.p. 67°
5. 5-(4-chloro-2-nitrobenzoyl)-7a-methyl-2,3,7,7a-tetrahydro-1H-indene-4,6(5H)-dione, in oil
6. 5-(4-chloro-2-methylbenzoyl)-2,3,7,7a-tetrahydro-1H-indene-4,6(5H)-dione
7. 5-(4-chloro-2-trifluoromethylbenzoyl)-2,3,7,7a-tetrahydro-1H-indene-4,6(5H)-dione
8. 5-(2-methoxy-4-nitrobenzoyl)-2,3,7,7a-tetrahydro-1H-indene-4,6(5H)-dione
9. 5-(4-fluoro-2-methylsulfonylbenzoyl)-2,3,7,7a-tetrahydro-1H-indene-4,6(5H)-dione

EXAMPLE 3

A solution of compound 3 (2.54 mmol) and 2 drops of conc. sulfuric acid in 20 ml of methanol is heated under reflux for 48 hours. The reaction mixture is concentrated and the residue is taken up in ether. The ethereal solution is washed with aqueous sodium bicarbonate and with brine, dried and evaporated to dryness to give 4-methoxy-5-(4-chloro-2-nitrobenzoyl)-2,3,7,7a-tetrahydro-1H-indene-6-one and 6-methoxy-5-(4-chloro-2-nitrobenzoyl)-2,3,7,7a-tetrahydro-1H-inden-4-one.

EXAMPLE 4

To a mixture of compound 4 (2.26 mmol) in methylene chloride (10 ml) containing triethylamine (0.47 ml, 3.39 mmol) is added dropwise at 0° a solution of acetyl chloride (0.27 g, 3.39 mmol) in 5 ml of methylene chloride. The resulting mixture is stirred for 30 min., and is then diluted with methylene chloride, washed, dried and evaporated to dryness to give 4-acetoxy-5-(4-chloro-2-nitrobenzoyl)-7-methyl-2,3,7,7a-tetrahydro-1H-inden-6-one and 6'acetoxy-5-(4-chloro-2-nitrobenzoyl)-7-methyl-2,3,7,7a-tetrahydro-1H-inden-4-one.

The starting compounds of formula IIa and IIb herein are known or, in cases where they are novel, can be produced by methods analogous to known methods or by methods described herein.

Thus, the enol esters of formula IIa and IIb can be prepared by the reaction of a bicycloalkyl-1,3-dione of formula III (wherein $R^1$–$R^3$ are defined as hereinabove) with a benzoyl halide of formula IV (wherein Q is a halogen atom and $R^4$–$R^6$ are as defined hereinabove) in the presence of a moderate base such as triethylamine.

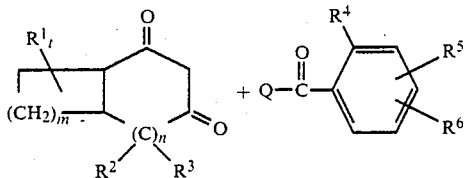

(III)   (IV)

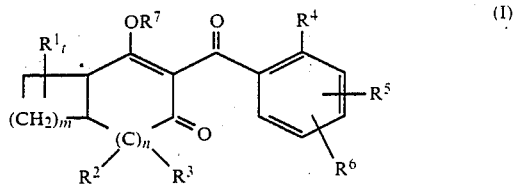

(I)

The diones of formula III can be prepared, for example, by reacting an acetylcycloalkene of formula V with a substituted diethyl malonate of formula VI to give a compound of formula III where n is one.

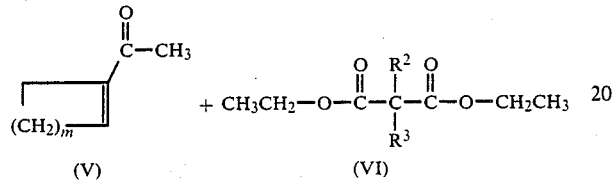

(V)   (VI)

PREPARATION OF INTERMEDIATE COMPOUNDS

The following examples are presented to illustrate representative methods of preparing the intermediate compounds.

EXAMPLE 5

Sodium metal (2.31 g, 101.0 mmol) is dissolved in 50 ml of ethanol, and diethyl methylmalonate (17.6 g, 101.0 mmol) is added, after which the mixture is stirred for approx. 30 min. under reflux. 1-Acetyl-1-cyclohexene (12.50 g, 101.0 mmol) is added and the mixture is stirred under reflux overnight. Potassium hydroxide (12.47 g, 222.2 mmol) dissolved in 40 ml of water is added and the mixture is heated under reflux for 4 hr. The ethanol is removed by rotary evaporation, and the residue is dissolved in water and washed with ether. The aqueous layer is acidified with conc. HCl and extracted with ether. The combined extracts are dried and the solvent is removed to give 4a,5,6,7,8,8a-hexahydro-4-methyl-naphthalene-1,3(2H,4H)-dione.

To a mixture of the above dione (8.0 g, 44.4 mmol) and 4-chloro-2-nitrobenzoyl chloride (44.4 mmol) in 50 ml of methylene chloride is added, dropwise, triethylamine (8.04 ml, 1.3 equiv.), and the mixture is stirred at RT for 2 hr. The reaction mixture is diluted with methylene chloride, washed with water and evaporated to give 1-(4-chloro-2-nitrobenzoyloxy)-4a,5,6,7,8,8a-hexahydro-4-methyl-3(4H)-naphthalenone and 3-(4-chloro-2-nitrobenzoyloxy)-4a,5,6,7,8,8a-hexahydro-4-methyl-1(4H)-naphthalenone.

EXAMPLE 6

Following the procedure of Example 5, the sodium salt of diethyl malonate (161.0 mmol) and 1-acetyl-2-methyl-1-cyclopentene (20.0 g, 161.0 mmol) are reacted together to give 7a-methyl-2,3,7,7a-tetrahydro-1H-indene-4,6(5H)-dione, which is then reacted with 4-chloro-2-nitrobenzoyl chloride (1 equiv.) to give 4-(4-chloro-2-nitrobenzoyloxy)-7a-methyl-2,3,7,7a-tetrahydro-1H-inden-6-one and 6-(4-chloro-2-nitrobenzoyloxy)-7a-methyl-2,3,7,7a-tetrahydro-1H-inden-4-one.

What is claimed is:

1. A compound of the following formula (I):

wherein, $R^1$ is $C_{1-8}$alkyl;

each of $R^2$ and $R^3$ is, independently, hydrogen, $C_{1-8}$alkyl or $COOR^8$;

$R^4$ is $C_{1-8}$alkyl, optionally substituted with one to six halogen atoms; $C_{1-8}$alkoxy, optionally substituted with one to six halogen atoms; $S(O)_{n'}R^{10}$; halogen; or nitro;

each of $R^5$ and $R^6$ is, independently, hydrogen; halogen; $C_{1-8}$alkyl, optionally substituted with one to six halogen atoms; $C_{1-8}$alkoxy, optionally substituted with one to six halogen atoms; $C_{1-8}$alkylcarbonyl; $C_{1-8}$alkoxycarbonyl; $NR^8R^9$; $SO_2NR^8R^9$; $S(O)_{n'}R^{10}$; nitro; or cyano; with the proviso that neither of $R^5$ nor $R^6$ is attached to the 6 position;

$R^7$ is hydrogen, $C_{1-8}$alkyl, $C_{1-8}$alkylcarbonyl, $C_{1-8}$alkoxycarbonyl, $C(O)NR^8R^9$, $C_{1-8}$alkylsulfonyl, $P(O)-(OR^{11})_2$ or $R^8P(O)OR^{11}$;

each of $R^8$ and $R^9$ is, independently, hydrogen or $C_{1-8}$alkyl;

$R^{10}$ is $C_{1-8}$alkyl, optionally substituted with one to six halogen atoms;

$R^{11}$ is $C_{1-8}$alkyl;

m is zero to three;

n is zero or one;

n' is zero, one or two; and t is zero to six.

2. A compound according to claim 1 wherein n is zero; $R^1$ is $C_{1-4}$alkyl, each of $R^2$ and $R^3$ is independently hydrogen or $C_{1-4}$alkyl, and $R^6$ is hydrogen.

3. A compound according to claim 2 wherein $R^4$ is (a) $C_{1-4}$alkyl optionally substituted with one to three halogen atoms, (b) $C_{1-4}$alkyl-$S(O)_{n'}$, (c) halogen, or (d) nitro; and $R^5$ is (a) hydrogen, (b) $C_{1-4}$alkyl optionally substituted with one to three halogen atoms, (c) $C_{1-4}$alkyl-$S(O)_{n'}$, (d) halo$C_{1-4}$alkyl-$S(O)_{n'}$, (e) $C_{1-4}$alkoxy optionally substituted with one to three halogen atoms, (f) halogen, or (g) nitro, and is in the 4 position.

4. A compound according to claim 3 wherein m is two or three.

5. A compound according to claim 4 wherein $R^4$ is methyl, trifluoromethyl, methylsulfonyl, bromo, chloro or nitro and $R^7$ is hydrogen.

6. A compound according to claim 5 wherein $R^5$ is hydrogen, methoxy, trifluoromethyl, $C_{1-3}$alkylsulfonyl, halo$C_{1-3}$alkylsulfonyl, chloro, fluoro or nitro.

7. A compound according to claim 6 wherein t is zero, one or two; $R^1$ is methyl or ethyl; and each of $R^2$ and $R^3$ is independently hydrogen, methyl or ethyl.

8. A compound according to claim 7 wherein $R^4$ is nitro.

9. A compound according to claim 8 wherein $R^5$ is chloro.

10. A compound according to claim 9 wherein m is two.

11. A method for the control of weeds which comprises treating the weed or its locus with a herbicidally effective amount of a compound of formula I as defined in claim 1.

12. A compound according to claim 1 wherein m is 2, n is 1, t is 0, $R_2$, $R_3$, $R_6$ and $R_7$ are hydrogen, $R_4$ is nitro and $R_5$ is 4-chloro.

* * * * *